United States Patent [19]

Stults et al.

[11] Patent Number: 5,166,404
[45] Date of Patent: Nov. 24, 1992

[54] DIOXYDIPHTHALIC ACID ESTERS

[75] Inventors: Jeffrey S. Stults; Willis T. Schwartz, both of Grand Island; Frank J. Dinan, Tonawanda, all of N.Y.

[73] Assignee: Occidental Chemical Corporation, Niagara Falls, N.Y.

[21] Appl. No.: 771,713

[22] Filed: Oct. 4, 1991

Related U.S. Application Data

[60] Continuation-in-part of Ser. No. 621,412, Dec. 3, 1990, Pat. No. 5,089,631, which is a division of Ser. No. 492,196, Mar. 13, 1990, Pat. No. 5,003,086, which is a division of Ser. No. 352,070, May 15, 1989, Pat. No. 4,943,642.

[51] Int. Cl.$^5$ .................. C07C 63/331; C07C 69/80
[52] U.S. Cl. .................... 560/65; 549/359; 562/474
[58] Field of Search ............ 549/359; 560/65; 562/474

[56] References Cited

U.S. PATENT DOCUMENTS 3,879,428  4/1975  Heath et al. ............... 260/346.3
4,697,023  10/1986  Schwartz et al. ............ 549/241

FOREIGN PATENT DOCUMENTS 2416594  12/1983  Fed. Rep. of Germany .

OTHER PUBLICATIONS

Kolesnikov, G. S. et al Volsokomol. Soyed, A9, 612-18 (1967).
Marvel, C. S. et al, J. Am. Chem. Sco., 80, 1197 (1958).
Lavrova, Z. N. et al, Volokna Sin. Polim., 15-24, (1970).
Tilika et al., Synthesis of Carboxylic Acids of Aromatic Sulfides Latv. PSR Zinat. Akad. Vestis, Kim. Ser.(2), 201-4, 1982 (CA 97(7):55412U.
Pebalk et al, Spin Density Distribution . . . Dikl. Akad. Nauk, SSR, 244(5), 1169-73 (Phys. Chem.) 1979 (CA 90(23):186029c.
Pebalk et al, Electron-acceptor Properties of Aromatic Dianhydrides Dokl. Akad. Nauk, SSR, 236(6), 1379-82 (Chem.) 1977 (CA 88(19):135960a.
Erglis et al, (USSR Patent No. 395,358) CA 89(9):48007m (1974).
Govindachari et al, Chemical Abstracts, vol. 67 (1967) 54088m.

Primary Examiner—Richard L. Raymond
Attorney, Agent, or Firm—Arthur S. Cookfair

[57] ABSTRACT

Oxydiphthalic acid esters of the formula

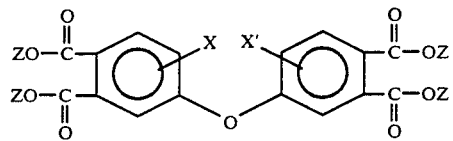

where Z is H or alkyl, and X is halo, X' is H or halo, or X and X' together represent an oxygen atom; are prepared by the esterification reaction of the corresponding halo-oxydiphthalic anhydride or dioxydiphthalic anhydride with an alkanol.

1 Claim, No Drawings

DIOXYDIPHTHALIC ACID ESTERS

This is a continuation in part of application Ser. No. 07/621,412, filed Dec. 3, 1990, now U.S. Pat. No. 5,089,631; which is a division of application Ser. No. 07/492,196, filed Mar. 13, 1990, now U.S. Pat. No. 5,003,086; which is a division of application Ser. No. 07/352,070, filed May 15, 1989, now U.S. Pat. No. 4,943,642.

BACKGROUND OF THE INVENTION

This invention relates to novel tetraacid ester compounds derived from halo-oxy- or dioxyphthalic anhydrides. The products are useful chemical intermediates for the further preparation of various compounds such as the corresponding tetracarboxylic acids and the various derivatives thereof. The esters of this invention are particularly useful as industrial plasticizers for polyvinyl chloride and polystyrene resins. Especially useful for this purpose are the alkyl esters, wherein the alkyl chain is 7-9 carbon atoms. Dioxydiphthalic diesters, wherein ester groups are on opposite phthalic acid groups are useful in the preparation of polyimides.

U.S. Pat. No. 4,697,023 discloses the preparation of oxydiphthalic anhydrides and suggests their use in the preparation of polyimides. The oxydiphthalic anhydrides are prepared by the reaction of a halophthalic anhydride with water and an alkali metal compound such as KF, CsF, or $K_2CO_3$ in the presence of a polar aprotic solvent.

Kolesnikov, G. S. et al, *Vysokomol. Soyed*, A9, 612-18 (1967); Marvel, C. S. et al, *J. Am. Chem. Soc.*, 80, 1197, (1958); and Latrova, Z. N. et al, *Volokna Sin. Polim.*, 15-24 (1970), disclose the preparation of oxydiphthalic acids and anhydrides by the oxidation of tetramethyldiphenyl ethers.

German patent No. 2,416,594 (1975) discloses the preparation of 3,3'-oxydiphthalic anhydride by coupling of 3-nitrophthalic anhydride in the presence of metal nitrites such as sodium nitride.

U.S. Pat. No. 3,879,428 to Heath et al discloses the preparation of various aromatic bis(ether anhydrides) by reaction of nitrophthalimide with an alkali diphenoxide followed by hydrolysis and dehydration to yield the diether anhydride.

Tilika et al, Synthesis of Carboxylic Acids of Aromatic Sulfides, Latv. PSR Zinat. Akad. Vestis, Kim. Ser. (2), 201-4, 1982; CA 97(7):55412U, disclose the reaction of 5-bromo-4-mercaptophthalic acid with $Cu_2O$ to give 80 percent thianthrene-2,3,7,8-tetracarboxylic acid, that is,

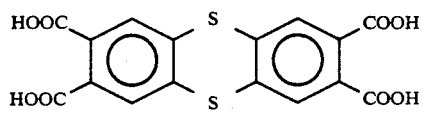

Pebalk et al, Spin Density Distribution In Anion Radicals of Aromatic Tetracarboxylic Acid Dianhydrides, Dokl. Akad Nauk, SSR, 244(5), 1169-73, [Phys. Chem.] 1979; CA 90(23):186029c, disclose the EPR spectra of various compounds including a compound of the structure

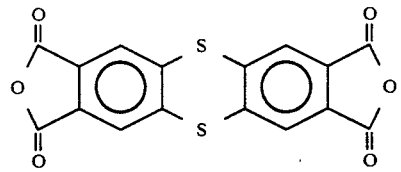

Pebalk et al, Electron-acceptor Properties of Aromatic Dianhydrides, Dokl. Akad. Nauk, SSR, 236(6), 1379-82, [Chem.] 1977; CA 88(19):135960a, disclose the electron-acceptor properties of 15 phthalic anhydrides and condensed phthalic anhydrides including dithiodiphthalic anhydrides.

2,3,7,8-Tetracarboxyphenoxathin dianhydride of the formula

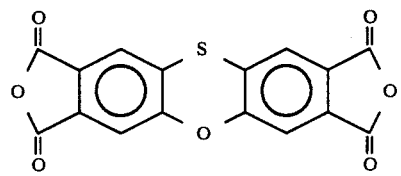

is disclosed by Erglis et al., (USSR Patent No. 395,358; CA 80(9):48007m). The compound was prepared by the reaction of $(3,4\text{-}Me_2C_6H_3)_2O$ with sulfur in the presence of aluminum chloride followed by oxidation with $KMnO_4$ in aqueous piperidine to form the tetracarboxylic acid, which was cyclized.

SUMMARY OF THE INVENTION

The present invention relates to new oxydiphthalic tetraacid esters of the formula

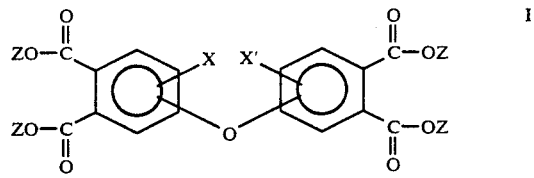

where each Z is independently H or an alkyl group of 1-12 carbon atoms, X is F, Cl, Br or I, X' is H, F, Cl, Br or I, or X and X' may together represent an oxygen atom forming a second ether linkage, with the proviso that when X and X' are taken together to represent an oxygen atom, the ether linkage is positioned at ring carbon sites adjacent to the sites forming the first ether linkage shown.

DETAILED DESCRIPTION OF THE INVENTION

The oxydiphthalic tetraacid esters of the present invention can be conveniently prepared by the esterification reaction of the corresponding halo-oxydiphthalic or dioxydiphthalic anhydride with a suitable alkanol, for example, by heating and maintaining a mixture of the anhydride and alkanol at reflux conditions for several hours. The halo-oxydiphthalic or dioxydiphthalic anhydrides employed are characterized by the formula

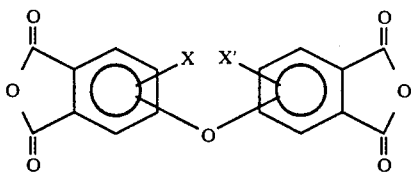

II where X is F, Cl, Br or I, X' is H, F, Cl, Br or I or X and X' may together represent an oxygen atom forming a second ether linkage with the proviso that the second ether linkage is positioned at ring carbon sites adjacent to the sites forming the first ether linkage shown. These starting halo-oxydiphthalic or dioxydiphthalic anhydrides can be prepared by reacting a dihalophthalic anhydride of the formula

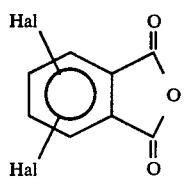

III where Hal is F, Cl, Br, or I with water and an alkali metal compound selected form the group consisting of KF, CsF, and $K_2CO_3$.

In the process, the halogen atoms on the dihalophthalic anhydride reactant function as leaving groups and become the site for the formation of an ether bridge. Thus, when the reactant is a 4,5-dihalophthalic anhydride such as

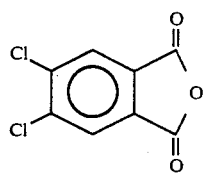

IV the reaction products will include 4,4'-dihalo-5,5'-oxydiphthalic anhydride, characterized by the formula

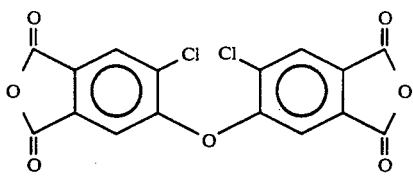

V and 4,,4',5,5'-dioxydiphthalic anhydride characterized by the formula

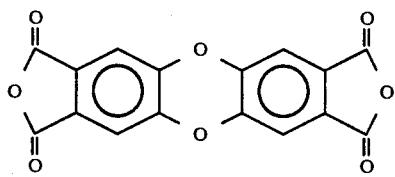

VI

The particular halogen atoms at the 4 and 4' positions will depend on the halogen atoms present at the 4 or 5 position of the starting dihalophthalic anhydride. Thus, for example, the above oxydichlorodiphthalic anhydride (IV) may be formed from 4,5-dichlorophthalic anhydride starting material. When difluorophthalic anhydride is employed, the corresponding difluoro-oxydiphthalic anhydride may be formed. In addition, a mono-chloro-oxydiphthalic anhydride may be formed by using as a starting reactant a mixture of a monohalophthalic anhydride, such as 4-chlorophthalic anhydride and a dihalophthalic anhydride, such as 4,5-dichlorophthalic anhydride. Furthermore, the ring site of the oxygen bridge(s) as well as the ring site dianhydride produced, may be varied by selective choice of the halophthalic anhydride reactant employed.

While not being bound by any particular theory, it is believed that the oxy-dihalo-diphthalic anhydride is formed as an intermediate during the initial stages of reaction. The percentage yield thereof may be enhanced by limiting the time of reaction. Alternatively, by increasing the reaction time, the dioxydiphthalic anhydride is produced essentially as the sole product. The amount of halo-substituted oxydiphthalic anhydride produced can be increased by limiting the ratio of water to dihalophthalic anhydride to less than 1:1. The halo-substituted oxydiphthalic anhydride is separable from the dioxydiphthalic anhydride by common physical separation means, such as selective recrystallization, etc. The dihalo-oxydiphthalic anhydrides are useful as monomers in the preparation of polyimides. Bromo- and/or chloro-substituted dianhydrides may be employed to enhance the fire retardant properties of polyimides prepared therefrom. Fluoro-substituted dianhydrides, prepared for example from difluoro-phthalic anhydride may be employed to improve electrical properties, such as dielectric strength of polyimides. In addition, the presence of fluorine ring substituents should increase the solubility of the polyimide in common solvents.

When the reactant is 3,4-dihalophthalic anhydride, the dioxydiphthalic anhydride product formed will be 3,3',4,4'-dioxydiphthalic anhydride which, upon esterification, will form a tetracarboxylic acid ester, characterized by the formula

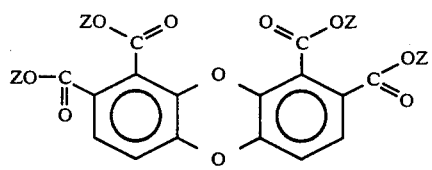

VII

Alternatively, a mixture of the 3,4-dihalo- and 4,5-dihalo-phthalic anhydrides may be employed as the starting reactant to form a dioxydiphthalic anhydride which, upon esterification, will form a tetracarboxylic acid ester of the formula

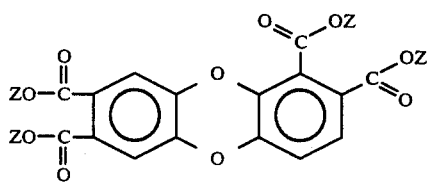

VIII

The halogen substituents on the starting halophthalic anhydride reactant may be F, Cl, Br or I. The preferred reactant is 4,5-dichlorophthalic anhydride.

The tetraalkyl esters, especially the tetraethyl ester of 4,4′-dihalo-5,5′-oxydiphthalic anhydride, for example of the formula

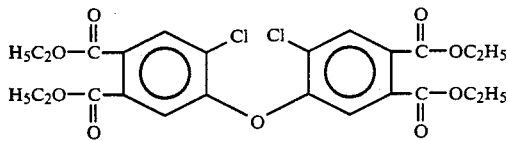

may be reacted with Na$_2$S to form the tetraester of 2,3,7,8-tetracarboxyphenoxathin, for example, the tetraethyl ester of the formula

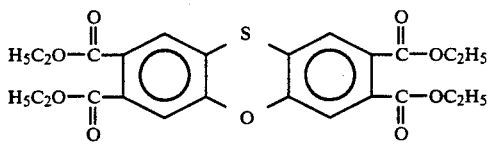

In the preparation of the diphthalic anhydride, the alkali metal compound reactant may be potassium fluoride, cesium fluoride, or potassium carbonate, the latter being preferred. The proportions of reactants may vary considerably. However, it is recommended that the alkali metal compound be employed in sufficient proportions to provide at least two equivalents of potassium (or cesium) per mole of dihalophthalic anhydride. Preferably, the alkali metal compound is employed in substantial stoichiometric excess.

In the preparation of dioxydiphthalic anhydride, water is a limiting reactant and ideally, for maximum efficiency, is preferably present in a molar proportion of H$_2$O:dihalophthalic anhydride of about 1.0. The water may be added to the initial reaction mixture or alternatively, may be generated in situ. For example, when potassium carbonate is employed in the reaction mixture, a trace amount of water may be present in the initial reaction mixture and additional water generated in situ as the reaction proceeds.

The process of the invention is preferably carried out at atmospheric pressure, but super-atmospheric pressure, for example under autogenous conditions may be employed, if desired.

The process is preferably carried out neat. However, a solvent may be employed. The preferred solvents are polar, aprotic solvents such as N-methyl pyrrolidone, dimethyl formamide, dimethyl acetamide, triglyme, sulfolane, or the like, the most preferred solvent being sulfolane.

The temperature at which the process is carried out may vary considerably, but will generally be within the range of about 120° to about 230° C. Higher or lower temperatures may be employed, but are less preferred. If a solvent is employed, the choice of the solvent may govern the temperature employed. For example, at atmospheric conditions the boiling point of the solvent may become a limiting condition.

In addition to the dianhydrides and esters prepared in accordance with the process described, this invention is also directed to the acids, acid chlorides, esters and salts derived therefrom. Such derivatives are readily prepared by known reactions. For example, the dianhydride may be converted to the tetracarboxylic acid by hydrolysis and the tetracarboxylic acid may be converted to the corresponding acyl chloride by reaction with a suitable inorganic acid chloride such as thionyl chloride, phosphorus trichloride, or phosphorus pentachloride. The acid chloride may, in turn, be reacted with amines to form amides, diamides or imides, depending on stoichiometry and reaction conditions. If diamines are employed, the corresponding polymers may be formed. Furthermore, the dianhydride may be reacted with ammonia to form the corresponding ammonium phthalamate, hydrolyzed to form phthalamic acid, and dehydrated to yield the corresponding diimide.

In accordance with the present invention, the dianhydride (or tetra-acid) may be reacted with alcohols to form novel mono-, di-, tri-, or tetracarboxylic acid esters. The reaction may be carried out over a wide range of temperatures; for example, from about room temperature (20° C.) to the reflux temperature of the reaction mixture, optionally in the presence of a catalyst, such as a mineral acid. Suitable catalysts include, for example, sulfonic acid, sulfuric acid, hydrochloric acid, and the like. The process may be carried out neat or in the presence of a solvent. Suitable solvents include, for example, polar aprotic solvents, such as sulfolane, dimethyl formamide, dimethylacetamide, N-methyl pyrrolidone, and the like. The reaction is preferably carried out at atmospheric pressure, at the boiling point of the reaction mixture, although higher temperatures may be employed under autogenous conditions.

Following the conditions set forth above, the process may be employed to prepare the monoesters, diesters and triesters as well as the tetraesters of dioxydiphthalic acid. While not being bound by any particular theory, it is believed that the lower esters, that is the mono-, di-, and tri-esters are formed sequentially, as intermediates, during the process. The percentage yield of the lower esters may be enhanced by limiting the time of reaction. Furthermore, since formation of the tri- and tetra- esters is a slow reaction, it is preferred to employ a catalyst, such as a mineral acid. The mono- di-, tri-, and tetraesters may be separated by common physical separation techniques, such as fractional crystallization and the like, or chemical separation methods, such as selective neutralization.

During the esterification reaction, the formation of the diester appears to take place preferentially with the formation of ester groups on opposite phthalic acid groups. The diester thus formed, that is having the two ester groups on opposite phthalic acid groups, may be used as an intermediate in the formation of mixed acid chloride esters, for example, of the structure

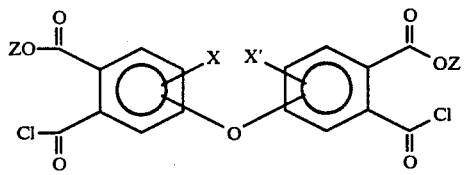

Mixed acid chloride esters such as those of the above structure, may be conveniently prepared, for example by reaction of the diester with oxalyl chloride in dimethylformamide. The mixed acid chloride esters may be reacted with diamines to give polyamic alkyl esters, which are stable polyimide precursors, readily convertible to polyimides by heating.

The monoanhydride diester, that is of the formula

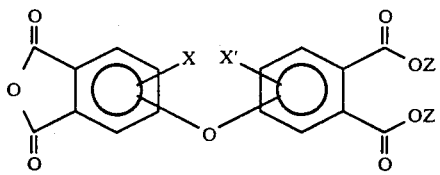

where X, X' and Z are as defined above, may be prepared from the triester by heating to about 200° C. or higher. The mono-anhydride diesters are useful as curing agents for epoxide resins and as end-capping monomers for polyimides. The monoimide diester may be formed from the mono-anhydride diester by reaction with ammonia or an amine. The mono-imide diesters are useful as plasticizers.

The following examples are provided to further illustrate the invention in the manner in which it may be carried out. It will be understood, however, that the specific details given in the examples have been chosen for purposes of illustration only and are not to be construed as limiting the invention. In the examples, unless otherwise indicated, all temperatures are in degrees Celsius.

EXAMPLE 1

Preparation of Dioxydiphthalic Anhydride

A solution of 21.7 grams (0.1 mole) of 4,5-dichlorophthalic anhydride in 40 grams of sulfolane was heated and maintained at 210°–215° C. while 0.215 grams of tetraphenylphosphonium bromide was added followed by the incremental addition of 13.82 grams (0.1 mole) of potassium carbonate over a period of about 4 hours. The temperature was maintained an additional hour and the reaction mixture was then cooled to room temperature. Acetone (100 ml) was added and mixed. The reaction mixture was filtered and the solids washed consecutively with another 100 ml of acetone, two 100 ml portions of water, and again with 100 ml of acetone, to yield about 15 grams of brown solid. After drying, the solid was recrystallized from about 225 grams of 1,2,4-trichlorobenzene to yield 12.5 grams of a tan colored crystalline solid. Mass spectral analysis indicated the product to have a molecular weight of 324 with a fragmentation consistent with dioxydiphthalic anhydride. The identification of dioxydiphthalic anhydride was confirmed by infra-red analysis and $C^{13}$ NMR (CP/MAS).

EXAMPLE 2

Preparation of Dioxydiphthalic Anhydride 4,5-Difluorophthalic anhydride (18.4 grams, 0.1 mole) was dissolved in 40 grams of anhydrous sulfolane and heated to 165° C. with stirring. Tetraphenylphosphonium bromide (0.184 grams, 0.0004 mole) and 1.8 grams (0.10 mole) of water were added and the temperature increased to 200° C. Anhydrous potassium fluoride (23.3 grams, 0.4 mole) was added with stirring. The reaction mixture was held at about 200° C. with stirring for about 3½ hours at which time another 0.2 grams of water was added and the reaction mixture was maintained at temperature for an additional hour. The reaction mixture was cooled to less than 150° C. and 35 grams of acetone added and the solids filtered off. The solids were washed with acetone followed by three 100 ml washes with distilled water. The solid material was dried at 150° C. for 16 hours to yield 15.5 grams (95.7% yield) of dioxydiphthalic anhydride.

EXAMPLE 3

Preparation of Dioxydiphthalic Acid

Dioxydiphthalic anhydride (3.0 g, 0.009 mole) was added to 95 g of water and heated to reflux. The dianhydride was dissolved by the addition of 4 ml of 40% NaOH. The resulting brown solution was decolorized with 0.2 g of activated carbon at reflux for 0.5 hour followed by filtration through celite. Acidifying with 12N HCl to a pH of less than 1 followed by a water wash and drying gave 1.9 g of product as confirmed by FTIR. DSC melting point was 260° C. with loss of water.

EXAMPLE 4

This example illustrates the manner in which 5-chloro-4,4'-oxydiphthalic anhydride may be prepared.

A solution of equal molar amounts of 4-chlorophthalic anhydride (18.2 g, 0.1 mole) and 4,5-dichlorophthalic anhydride (21.7 g, 0.1 mole) and tetraphenylphosphonium bromide (0.215 g) in 60 g of sulfolane is heated to 180°–210° C. Temperature is maintained, with stirring, while 0.05 mole (6.91 g) of potassium carbonate is added over a period of about one hour. The temperature is maintained for an additional two hours, then lowered to room temperature.

EXAMPLE 5

Potassium fluoride (5.04 g) and Carbowax MPEG 2000 (0.71 g) were added to and mixed with 10.2 g of a mixture of 56.1% (GC area percent) 4,5-difluorophthalic anhydride and 43.9% (GC area percent) 4-chloro-5-fluorophthalic anhydride. The powdery mixture was heated in a flask to 180° C., forming a viscous, paste-like reaction mixture. The temperature was maintained at 180°–207° C. for approximately 3.5 hours, during which a portion of the reaction mixture sublimed and condensed on the upper portion of the flask. The flask was cooled to room temperature and the sublimate collected (6.69 g) and analyzed by gas chromatography, indicating, in area percent, 74% 4,5-difluorophthalic anhydride and 26% 4-chloro-5-fluorophthalic anhydride. The reaction mixture remaining at the bottom of the flask (7.58 g) was analyzed by gas chromatography and found to contain in area percent, 50.1% 4,5-difluorophthalic anhydride; 42.8% 4-chloro-5-fluorophthalic anhydride; 3.4% 4,4'-difluoro-5,5'-oxydiphthalic anhydride; 2.1% 4-chloro-4'-fluoro-5,5'-oxydiphthalic anhydride; 0.3% 4,4'-dichloro-5,5'-oxydiphthalic anhydride and 1.0% 4,4',5,5'-dioxydiphthalic anhydride.

EXAMPLE 6

Preparation of the Tetraethyl Ester of Dioxydiphthalic Dianhydride 4,4',5,5'-Dioxydiphthalic anhydride (2.0 g) was added to 100 ml of absolute ethanol and 2.0 ml of concentrated sulfuric acid. The resulting mixture was refluxed for about 16 hours under an atmosphere of nitrogen. Approximately 50 ml of ethanol was removed by distillation and the resulting concentrated solution was poured into 300 ml of hot aqueous 5% sodium bicarbonate. The precipitated solids were filtered, rinsed with distilled water, and dried to give a crude yield of 2.6 g (88%) of the tetraethyl ester of dioxydiphthalic anhydride. Recrystallization form a 15% aqueous ethanol solution afforded 2.2 g (76% yield) of purified product as beige crystals, m.p. 114°-116° C.

When the general procedure of Example 6 is repeated, substituting other alkanols in place of ethanol, the corresponding esters are prepared. Moreover, when the reaction is carried out for shorter periods of time, a lower degree of esterification may occur and, by varying the time of reaction, increasing amounts of the triester, diesters, and monoester may be produced. The components of such a mixture may be separated by physical separation means, such as distillation, fractional crystallization, chromatographic techniques and the like. In some instances, a mixture of esters may be used without separation. Thus, for example, a mixture of esters such as octyl esters of dioxydiphthalic acid may be employed without separation as a plasticizer for polyvinyl chloride.

EXAMPLE 7

Preparation of diethylesters diacid of dioxydiphthalic anhydride 4,4',5,5'-Dioxydiphthalic anhydride (2.0 g) was added to 100 ml of absolute ethanol and 2 ml of concentrated sulfuric acid. The mixture was refluxed for 6.5 hours under an atmosphere of nitrogen, about 50 ml of ethanol was removed by distillation, and the resulting mixture was combined with 300 ml of hot aqueous sodium bicarbonate solution. Upon cooling, the mixture wa filtered. Acidification of the filtrate with 6 N HCl resulted in precipitation of a white/pink solid which was filtered, washed with water, and dried to give 0.89 g (35% yield) of diethylesters, diacid of dioxydiphthalic acid (m.p. 160°-200° C.).

What is claimed is:

1. An oxydiphthalic ester of the formula

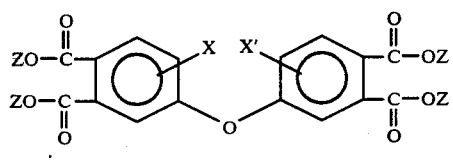

wherein each Z is independently H, or an alkyl group of 1-12 carbon atoms, X is F, Cl, or Br, and X' is H, F, Cl, or Br.

* * * * *